(12) United States Patent
Millet Aguilar-Galindo et al.

(10) Patent No.: US 10,420,755 B2
(45) Date of Patent: Sep. 24, 2019

(54) USE OF CICLOPIROX FOR THE TREATMENT OF CONGENITAL ERYTHROPOIETIC PORPHYRIA

(71) Applicant: ASOCIACIÓN CENTRO DE INVESTIGACIÓN COOPERATIVA EN BIOCIENCIAS-CIC bioGUNE, Derio, Vizcaya (ES)

(72) Inventors: Oscar Millet Aguilar-Galindo, Vizcaya (ES); Arantza Sanz Parra, Vizcaya (ES); Ana Laín Torre, Vizcaya (ES); Pedro David Urquiza Ortiz, Vizcaya (ES); Juan Manuel Falcón Pérez, Vizcaya (ES)

(73) Assignee: ASOCIACIÓN CENTRO DE INVESTIGACIÓN COOPERATIVA EN BIOCIENCIAS-CIC BIOGUNE, Derio, Vizcaya (ES)

( * ) Notice: Subject to any disclaimer, the term of this patent is extended or adjusted under 35 U.S.C. 154(b) by 0 days.

(21) Appl. No.: 16/326,215

(22) PCT Filed: Oct. 27, 2017

(86) PCT No.: PCT/EP2017/077570
§ 371 (c)(1),
(2) Date: Feb. 17, 2019

(87) PCT Pub. No.: WO2018/078081
PCT Pub. Date: May 3, 2018

(65) Prior Publication Data
US 2019/0183871 A1 Jun. 20, 2019

(30) Foreign Application Priority Data
Oct. 28, 2016 (EP) ...................... 6382493

(51) Int. Cl.
*A61K 31/4412* (2006.01)
*A61P 3/00* (2006.01)

(52) U.S. Cl.
CPC ............ *A61K 31/4412* (2013.01); *A61P 3/00* (2018.01)

(58) Field of Classification Search
CPC ................................................ A61K 31/4412
See application file for complete search history.

(56) References Cited

FOREIGN PATENT DOCUMENTS

WO    WO2012017088 A1    2/2012

OTHER PUBLICATIONS

Tauber et al., Comparison of the Antifungal Efficacy of Terbine Hydrochloride and Ciclopirox Olamine Containing Formulations against the Dermatophyte Trichophyton rubrum in an Infected Nail Plate Model, 2014, Mol. Pharmaceutics, 11, pp. 1991-1996 (Year : 2014).*
Urquiza et al., Repurposing ciclopirox as a pharmacological chaperone in a model of congenital erythropoietic porphyria, 2018, Sci Transl. Med., 10, eaat7467, pp. 1-9 (Year: 2018).*
Bdira, F.B., et al., "Tuning Intracellular Homeostatis of Human Uroporphyrinogen III Synthase by Enzyme Engineering at a Single Hotspot of Congenital Erythropoietic Porphyria", "Human Molecular Genetics", 2014, pp. 5805-5813, vol. 23, No. 21.
Blouin, J., et al., "Therapeutic Potential of Proteasome Inhibitors in Congenital Erythropoietic Porphyria", "PNAS", 2013, pp. 18238-18243, vol. 110, No. 45.
Di Pierro, E., et al., "Advances in Understanding the Pathogenesis of Congenital Erythropoietic Porphyria", "British Journal of Haematology", 2016, pp. 365-379, vol. 173.
Egan, D., et al., "Inducing Iron Deficiency Improves Erythropoiesis and Photosensitivity in Congenital Erythropoietic Porphyria", "Blood", 2015, pp. 257-261, vol. 126, No. 2.
Fortian, A., et al., "Uroporphyrinogen III Synthase Mutations Related to Congenital Erythropoietic Porphyria Identify a Key Helix for Protein Stability", "Biochemistry", 2009, pp. 454-461, vol. 48.
Fortian, A., et al., "Intracellular Rescue of the Uroporphyrinogen III Synthase Activity in Enzymes Carrying the Hotspot Mutation C73R", "Journal of Biological Chemistry", Apr. 15, 2011, pp. 13127-13133, vol. 286, No. 15.
Shoolingin-Jordan, P., et al., "Coupled Assay for Uroporphyrinogen III Synthase", "Methods in Enzymology", 1997, pp. 327-336, vol. 281.
Urquiza, P., et al., "New Pharmacological Therapies Against Congenital Erythropoietic Porphyria (CEP)", "Protein Science", 2015, p. 64 vol. 24, No. Suppl. 1.

* cited by examiner

Primary Examiner — Jeffrey S Lundgren
Assistant Examiner — Tori Strong
(74) Attorney, Agent, or Firm — Hultquist, PLLC; Steven J. Hultquist

(57) ABSTRACT

The present invention relates to the use of the compound ciclopirox or a pharmaceutically acceptable salt or solvate thereof for the treatment and/or prevention of congenital erythropoietic porphyria (CEP).

6 Claims, 3 Drawing Sheets
(3 of 3 Drawing Sheet(s) Filed in Color)

USE OF CICLOPIROX FOR THE TREATMENT OF CONGENITAL ERYTHROPOIETIC PORPHYRIA

CROSS-REFERENCE TO RELATED APPLICATIONS

This application is a U.S. national phase under the provisions of 35 U.S.C. § 371 of International Patent Application No. PCT/EP17/77570 filed Oct. 27, 2017, which in turn claims priority of European Patent Application No. EP16382493.1 filed Oct. 28, 2016. The disclosures of such International Patent Application No. PCT/EP17/77570 and European Patent Application No. EP16382493.1 priority patent application are hereby incorporated herein by reference in their respective entireties, for all purposes.

FIELD OF THE INVENTION

The present invention relates to compounds that increase the catalytic activity of uroporphyrinogen III synthase, showing potency for the treatment and/or prevention of congenital erythropoietic porphyria (CEP).

BACKGROUND OF THE INVENTION

The group of pathologies produced by a lack of activity in some of the enzymes of the heme group biosynthesis is generically known as porphyria. Normally the loss of activity is produced by mutations in the amino acid sequence of said proteins and the type of porphyria depends on the specific enzyme causing the mutation. The heme group biosynthesis is shown in Scheme 1 indicating the enzymes involved in each stage of the pathway (above the reaction arrow) and detailing the names of the specific pathologies caused by functioning deficiencies in each of these enzymes (in italic form) [P=propionate, A=acetate, V=vinyl, M=methyl].

Scheme 1: the heme biosynthetic pathway and its relationship with the porphyrias.

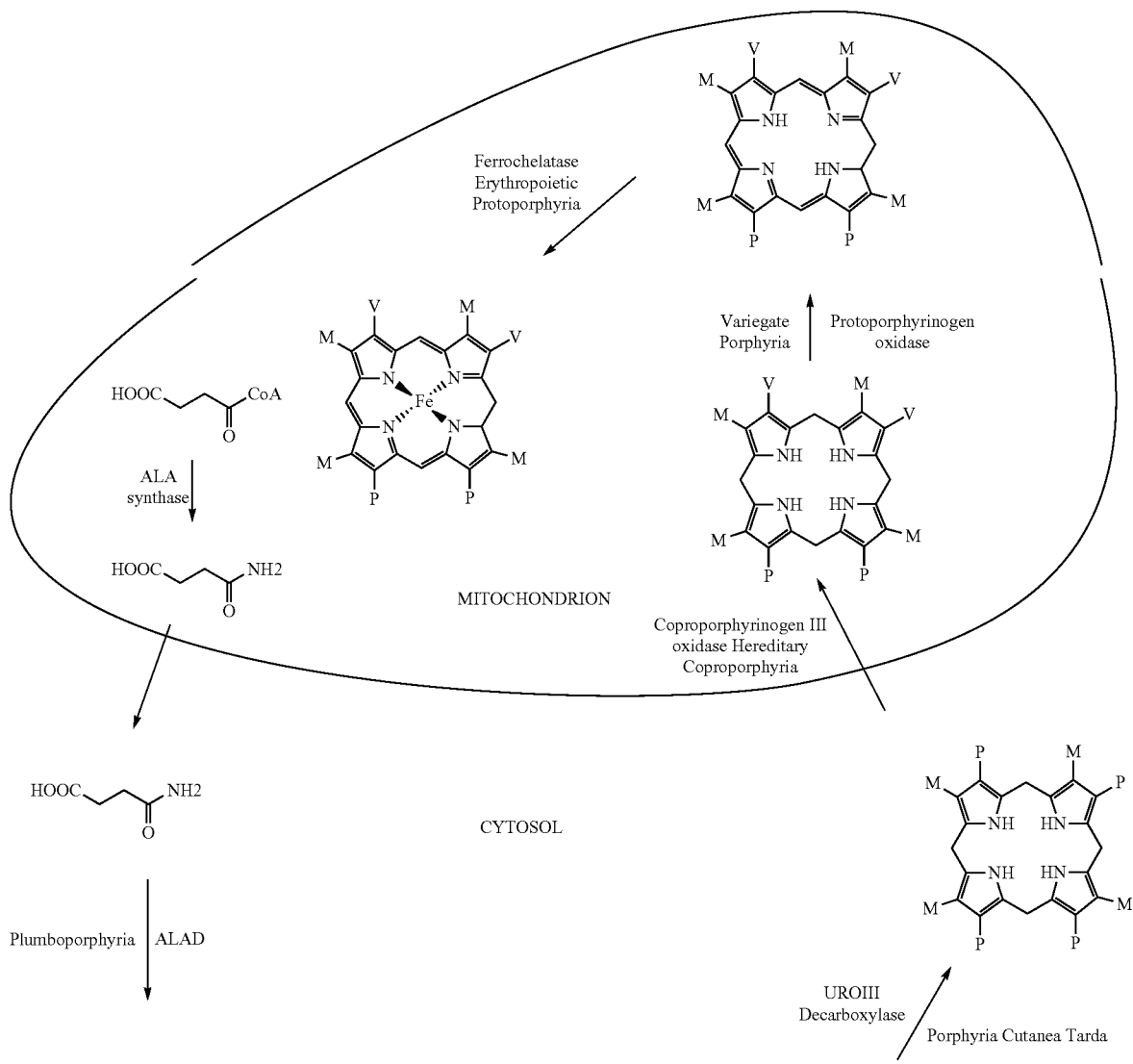

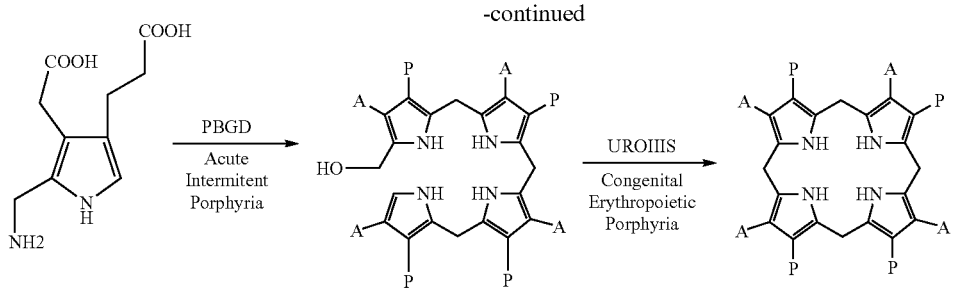

Congenital erythropoietic porphyria (CEP), also known as Günther's disease named after the author who described it in 1911, is a hereditary disease and the least frequent of the porphyrias (affecting >1 in 1000000 people). This disease is a consequence of a malfunction in the uroporphyrinogen III synthase (UROIIIS), which is an enzyme of 260 amino acid residues (in the human isoform) catalyzing the cyclization of the linear tetrapyrrole hydroxymethylbilane to produce macrocycle uroporphyrinogen III (or urogen III), the precursor of the heme groups, siroheme, F340, vitamin B12 and chlorophyll. The tetrapyrrole substrate is highly unstable and in the absence of the UROIIIS enzyme it spontaneously degrades to uroporphyrinogen I (uroporphyrinogen I and III differ only in the position of a P group and an A group in the D ring of the cycle). The cyclization of the preuroporphyrinogen for producing uroporphyrinogen III (enzymatic pathway) or uroporphyrinogen I (spontaneous degradation) is shown in Scheme 2.

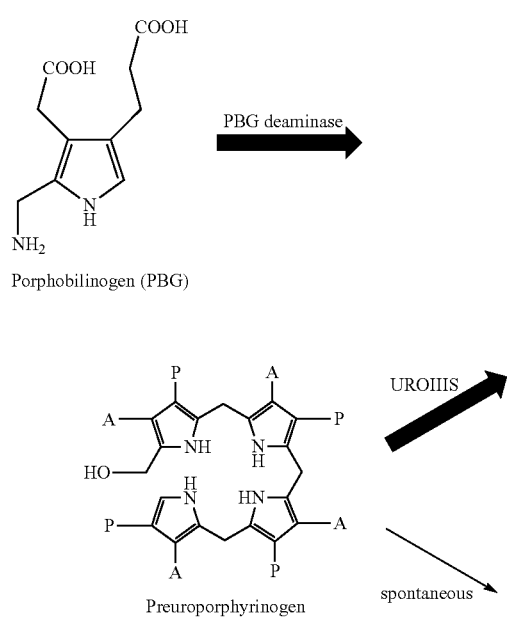

Uroporphyrinogen I and its derivatives are difficult to catabolize by-products that tend to accumulate in the body. Thus, large amounts of uroporphyrinogen I which accumulate in bags below the eyes and deform the extremities are produced in CEP patients (those having a UROIIIS deficiency). Depending on its severity, other common symptoms of the disease are, for example, an extreme sensitivity to sunlight from infancy that manifests as intense dermal lesions in the exposed areas, bone and cartilage destruction, erythrodontia (dark brown coloration of the teeth, especially baby teeth due to the porphyrin accumulation), anemia, splenomegaly produced by severe haemolytic anaemia, etc.

Some compounds have been proposed as useful for the management of CEP. For instance, WO 2012/017088 discloses pyrrole and indole compounds having capacity to inhibit the catalytic activity of porphobilinogen deaminase.

Today, however, the only curative treatment for CEP that has been reported is a bone marrow transplant, i.e., replacing the bone marrow of the CEP patient (recipient) with the healthy bone marrow of another person (donor). After an effective transplant the clinical characteristics of CEP, such as photosensitivity or anemia are resolved. However, the scars from previous skin lesions are permanent. Furthermore, for a successful transplant the bone marrow of the donor must have high similarity to that of the recipient. In this sense, the bone marrow transplant is a high-risk (two deceased cases in about fifteen transplants) and powerful treatments inhibiting the recipient's immune system are initially required to prevent rejection. Due to all of this, a bone marrow transplant is reserved for those severely affected individuals having an identical bone marrow donor.

Accordingly, there is still a great need of providing therapeutic agents suitable for the treatment and/or prevention of congenital erythropoietic porphyria (CEP).

SUMMARY OF THE INVENTION

Described herein is a novel treatment for congenital erythropoietic porphyria (CEP). In particular, we have demonstrated that the compound ciclopirox enhances the catalytic activity of uroporphyrinogen III synthase (UROIIIS) by increasing its stability and intracellular concentration levels. Further, the compound ciclopirox reduces the levels of uroporphyrinogen (UROI) and its derivatives in a relevant cellular model of the disease as well as in a murine model of CEP.

Therefore, in one aspect the present invention relates to ciclopirox or a pharmaceutically acceptable salt or solvate thereof for use in the treatment and/or prevention of CEP.

A further aspect is a pharmaceutical composition for use in the treatment and/or prevention of CEP comprising ciclopirox, or a pharmaceutically acceptable salt or solvate thereof, and a pharmaceutically acceptable excipient. According to a particular embodiment, said composition is for oral or topical administration.

Also is disclosed a method for the treatment and/or prevention of congenital erythropoietic porphyria (CEP) in a subject comprising the administration of a therapeutically effective amount of ciclopirox, or a pharmaceutically acceptable salt or solvate thereof to said subject. In a preferred embodiment, said subject is a human being.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
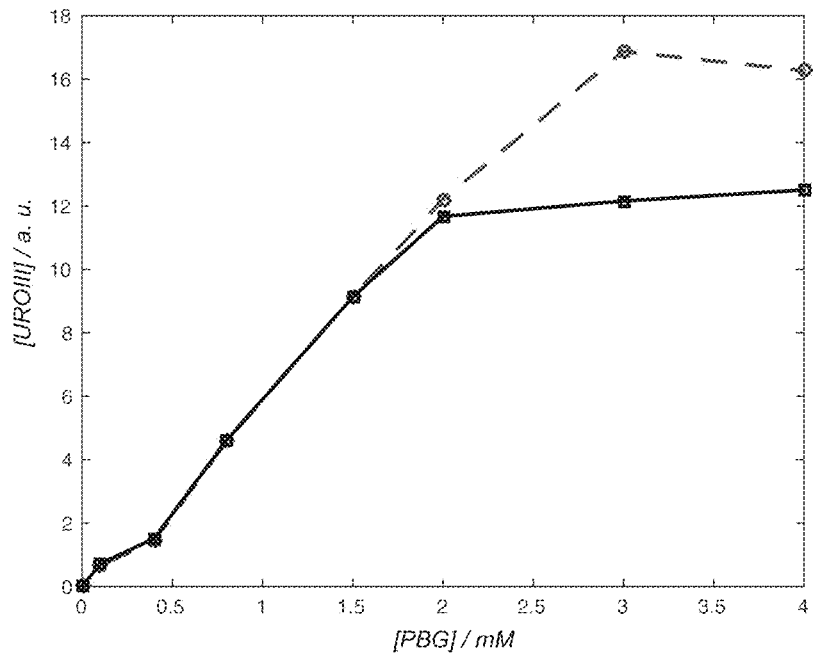
FIG. 1: evaluation of the C73N-UROIIIS catalytic activity as a function of the PBG concentration. Porphobilinogen deaminase (PBGD) converts porphobilinogen (PBG) into preuroporphirinogen, the substrate for UROIIIS. PBGD is added in excess, acting as a reagent and the experiment reports only on the catalytic activity of the uroporphyrinogen III synthase. The solid/dashed lines correspond to the experimental points in the absence/presence of ciclopirox at a ratio UROIIIS:ciclopyrox 1:5.

The compound ciclopirox was disclosed for the first time in the 1970s, in U.S. Pat. No. 3,883,545, where it was described as exhibiting antimycotic properties. The chemical name for ciclopirox is 6-cyclohexyl-1-hydroxy-4-methyl-2(1H)-pyridone, with the molecular formula $C_{12}H_{17}NO_2$ and a molecular weight of 207.27. The CAS Registry Number is [29342-05-0]. The chemical structure is depicted below in Scheme 3:

Scheme 3: ciclopirox

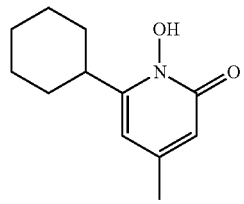

The present invention also contemplates all pharmaceutically acceptable salts and solvates of ciclopirox. For instance, ciclopirox can be for example ciclopirox olamine (CAS Registry Number [41621-49-2]), which comprises 6-cyclohexyl-1-hydroxy-4-methyl-2(1H)-pyridone with 2-aminoethanol in a 1:1 ratio.

Ciclopirox (and the salt ciclopirox olamine) have previously been described/used/approved as anti-fungal treatments. Currently, a variety of topical formulations indicated for the treatment of fungal infections are commercially available (e.g., as a lacquer, as a shampoo, as a solution, as a suspension, as a cream, as a lotion and as a gel).

Described herein is a new and surprising utility of the approved and commercially available drug ciclopirox. Specifically, in this invention it is demonstrated that ciclopirox is able to regulate the porphyrin concentration in a validated cellular model of CEP disease as well as in a mouse model of the pathology ($P248Q^{+/+}$). This activity is reported at extracellular concentrations that are comparable to the dosage administered for the already approved medical uses, thus indicating that the compound may be active at concentration below the toxicity threshold.

From the inventor's current data, the mechanism of action is believed to be based on the direct interaction with the enzyme driving the pathology of CEP, resulting in its stabilization.

There has been to the inventor's knowledge no disclosure of the utility of ciclopirox (or salts) in the treatment of CEP.

The present invention relates to the use of ciclopirox or a pharmaceutically acceptable salt or solvate thereof for the manufacture of a medicament for the treatment and/or prevention of CEP.

By "pharmaceutically acceptable" is meant herein a material that is not biologically or otherwise undesirable, i. e., the material may be incorporated into a pharmaceutical composition administered to a patient without causing any undesirable biological effects or interacting in a deleterious manner with any of the other components of the composition in which it is contained. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "salt" must be understood as any form of ciclopirox used according to this invention in which said compound is in ionic form or is charged and coupled to a counterion (a cation or anion).

Salts of ciclopirox may preferably be base addition salts or metallic salts, and they can be synthesized from the parent compound by conventional chemical methods. Examples of the alkali addition salts include inorganic salts such as, for example, ammonium, and organic alkali salts such as, for example, ethylenediamine, ethanolamine, triethanolamine, glucamine and basic aminoacids salts. Examples of the metallic salts include, for example, sodium, potassium, calcium, magnesium, aluminium and lithium salts. According to a particular embodiment, the salt of ciclopirox is a salt of alkali metals (for example of sodium or potassium); an ammonium salt; a primary amine salt (as for example $C_1$-$C_8$ alkyl amine); a secondary amine salt (as for example $C_1$-$C_8$ dialkyl amine); a tertiary amines salt (as for example $C_1$-$C_8$ trialkyl amine); a diamine salt; an alkanolamine salt (as for example $C_1$-$C_8$ alkanolamine or $C_1$-$C_8$ dialkanolamine or $C_1$-$C_8$ trialkanolamine); a $C_1$-$C_8$ dialkyl $C_1$-$C_8$ alkanolamine; or a $C_1$-$C_8$ alkyl $C_1$-$C_8$ dialkanolamine. A preferred ciclopirox salt is ciclopirox olamine.

The term "solvate" according to this invention is to be understood as meaning any form of the compound according to the invention in which this compound has attached to it via non-covalent binding another molecule (most likely a polar solvent) especially including hydrates and alcoholates, e.g. methanolate. Methods of solvation are generally known within the art.

According to an embodiment of the present invention, the compound ciclopirox or a pharmaceutically acceptable salt or solvate thereof is intended to increase the catalytic activity of uroporphyrinogen III synthase (UROIIIS).

According to another embodiment of the present invention, the compound ciclopirox or a pharmaceutically acceptable salt or solvate thereof is intended to increase the stability and concentration levels of uroporphyrinogen III synthase (UROIIIS).

According to another embodiment of the present invention, the compound ciclopirox or a pharmaceutically acceptable salt or solvate thereof is intended to reduce the toxic porphyrin levels, in particular the levels of uroporphyrinogen (UROI), coproporphyrinogen I (COPROI) and their derivatives.

According to another embodiment of the present invention, the compound ciclopirox or a pharmaceutically acceptable salt or solvate thereof is intended to alleviate or revert the lesions produced by the accumulation of porphyrin by-products in the skin, such as uroporphyrinogen (UROI) and its derivatives.

A further aspect is a pharmaceutical composition for use in the treatment and/or prevention of CEP comprising ciclopirox, or a pharmaceutically acceptable salt or solvate thereof, and a pharmaceutically acceptable excipient.

Examples of pharmaceutical compositions include any solid composition (e.g. tablets, pills, capsules, granules) or liquid composition (e.g. solutions, suspensions, lotions or emulsions).

The compositions can for example be administered orally, topically, dermally, nasally, intravenously, intramuscularly, intraperitoneally, intracerobrospinally, intracranially, intraspinally, subcutaneously, intraarticularly, intrasynovialy, or intrathecaly. Other forms of administration are not excluded. According to a particular embodiment, said composition is for oral or topical administration. According to another particular embodiment, said composition is formulated as a lacquer, as a shampoo, as a solution, as a suspension, as a cream, as a lotion or as a gel.

The respective composition may—depending on its route of administration—also contain one or more excipients known to those skilled in the art. The composition or medicament according to the present invention may be produced according to standard procedures known to those skilled in the art.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

As used herein, the terms "treat", "treating" and "treatment" include in general the eradication, removal, reversion, alleviation, modification, or control of CEP after its onset.

As used herein, the terms "prevention", "preventing", "preventive", "prevent" and "prophylaxis" refer to the capacity of a given substance, composition or medicament to avoid, minimize or difficult the onset or development of CEP before its onset.

Also is disclosed a method of treatment of a patient, notably a human, suffering CEP, or likely to suffer CEP, which comprises administering to the patient in need of such a treatment or prophylaxis an effective amount of ciclopirox, or a pharmaceutically acceptable salt or solvate thereof.

By an "effective" amount or a "therapeutically effective amount" of a drug or pharmacologically active agent is meant a nontoxic but sufficient amount of the drug or agent to provide the desired effect. In the therapy of the present invention, an "effective amount" of ciclopirox or a pharmaceutically acceptable salt or solvate thereof is the amount of that compound that is effective to provide the desired effect. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation.

Ciclopirox can be used together with other additional useful drugs in the prevention and/or treatment of congenital erythropoietic porphyria. Said additional drugs can form part of the same pharmaceutical composition or, alternatively, can be provided in the form of a separated composition for their simultaneous or sequential administration to that of the pharmaceutical composition comprising ciclopirox or a pharmaceutically acceptable salt or solvate thereof. For example, the treatment with ciclopirox or a pharmaceutically acceptable salt or solvate thereof could be complimented with the administration of heme derivatives or blood products to counteract the heme group deficiency.

The following examples are provided as supporting evidence for the invention since they demonstrate that the compound ciclopirox is able to increase the stability and concentration levels of UROIIIS and to reduce the toxic porphyrin levels in a relevant cellular model of the disease.

EXAMPLES

1. In Vitro Enzymatic Assay of UROIIIS:

The in vitro activity of a deleterious variant of the UROIIIS is measured as a function of the PBG concentration. This mutant (C73N-UROIIIS) has previously been demonstrated to produce a loss in the kinetic and thermodynamic stability of the enzyme (Fortian A, et al. Journal of Biological Chemistry, 2011). C73N-UROIIIS produces reduced catalytic activity of the enzyme (FIG. 1, solid line). In the presence of ciclopirox (ratio UROIIIS:ciclopirox 1:5), the enzyme recovers the enzymatic activity (FIG. 1, dashed line), thus demonstrating the pharmacological activity of ciclopirox. Direct binding has also been demonstrated using NMR spectroscopy.

Figure 2:
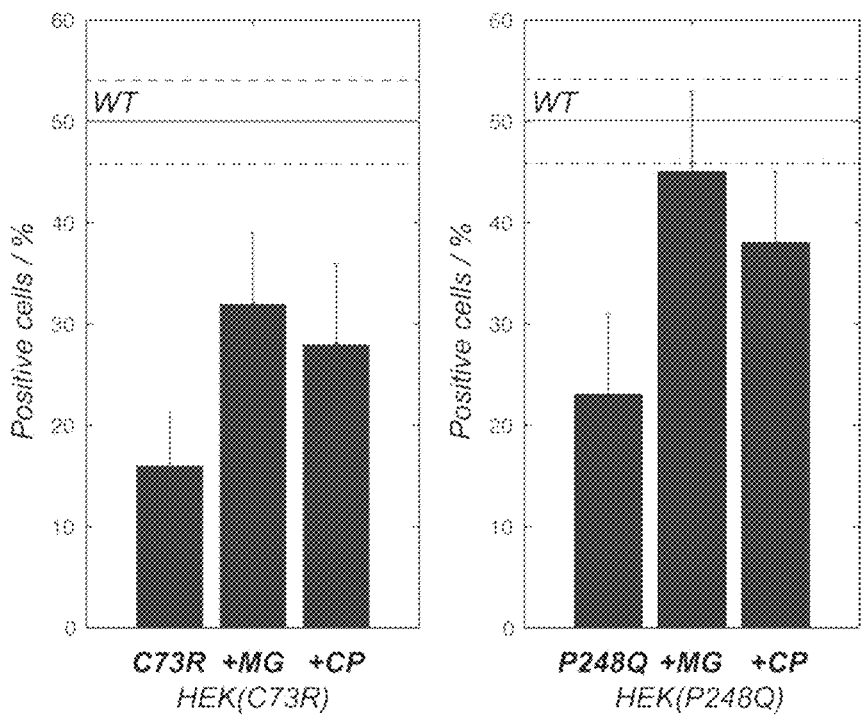
FIG. 2: A fusion construct with GFP (C73R-UROIIIS-GFP) has been stably expressed in HEK cells to measure the increase in the protein levels, by monitoring the intrinsic GFP fluorescence. The number of cells showing fluorescence are shown as bars while the horizontal solid line shows WT GFP fluorescence. Introduction of the pathogenic mutations (i. e. C73R or P248Q) reduces the intrinsic fluorescence due to a decrease in the intracellular UROIIIS concentration. The addition of ciclopirox (CP) largely restitutes the fluorescence levels observed with WT-UROIIIS. For comparison, data obtained with a powerful proteasome inhibitor (MG) is also included. Dashed lines correspond to error bars. CP=ciclopirox, MG=proteasomal inhibitor MG132.

2. Increased Homeostasis in Cellular Models:

We have demonstrated that the increased stability of UROIIIS following ciclopirox treatment observed in vitro, is also paralleled with enhanced concentration levels of UROIIIS protein in the cytosol of eukaryotic cells expressing some defective mutations of UROIIIS. Specifically, we have tested the protein expression for the two most aggressive mutations: C73R- and P248Q-UROIIIS (FIG. 2), utilising human embryonic kidney cells (HEK) stably expressing these mutations. For comparison, we have also performed supportive work using a tool compound (a proteasome inhibitor termed in the data MG) to demonstrate that the elevation of cellular levels of the UROIIIS enzyme result from improved homeostasis.

Figure 3:
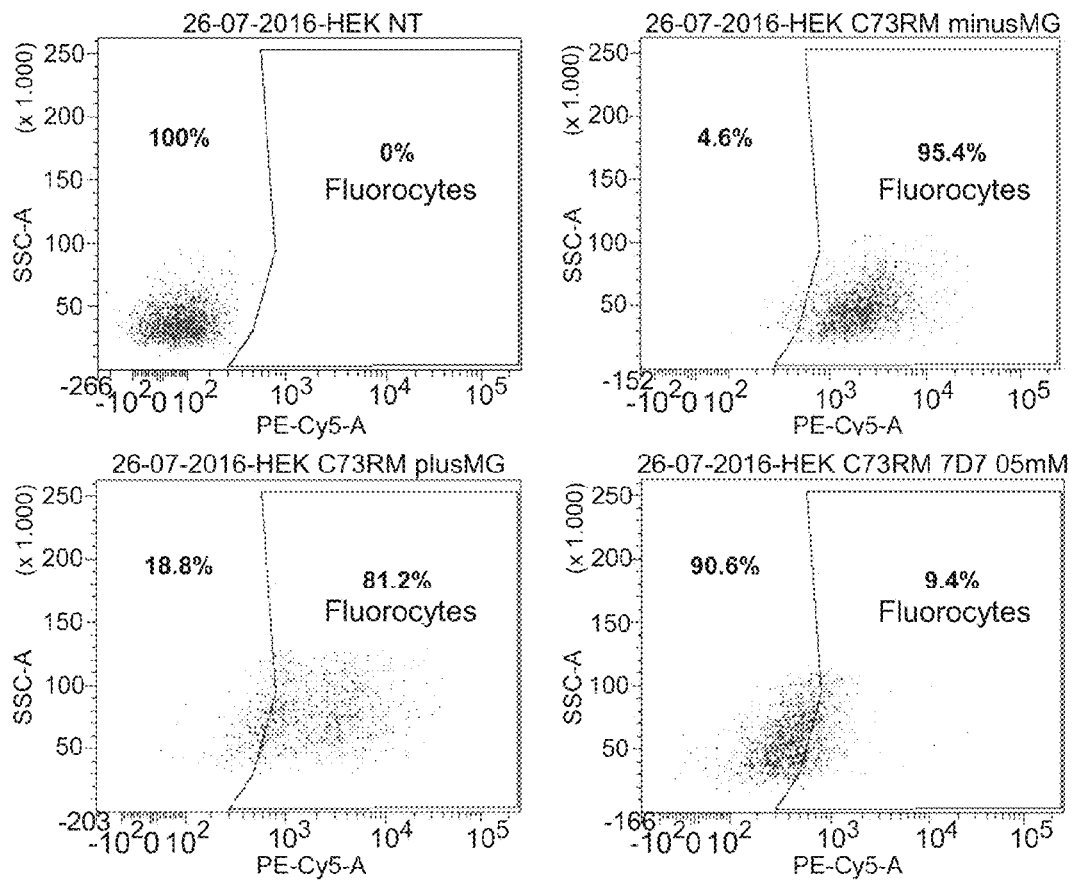
FIG. 3: Evaluation of UROI levels in a normal HEK cellular phenotype [Up-left graph], in a human in vitro cellular model of CEP (HEK 562) [Up-right graph], in HEK 562 with a tool compound (a proteasome inhibitor termed in the data MG) [Down-left graph], and in HEK 562 with ciclopirox [Down-right graph]. The accumulation of porphyrins is measured by fluorescence spectroscopy (fluorocytes) and is depicted in as the right-shift of the population as compared to normal cells (that are concentrated on the left due to the absence of intrinsic fluorescence). The numbers in bold indicate the percentage of cells in each of the specific populations. CP=ciclopirox, MG=proteasomal inhibitor MG132.

3. Ciclopirox Reduces UROI Levels in a Cellular Model of CEP:

The current supporting data disclosed is in relation to a human in vitro cellular model of CEP (HEK 562) in which there is a stable genomic defect introduced into the uroporphyrinogen III synthase enzyme which drives the accumulation of toxic porphyrins and ultimately the pathology of CEP (including the characteristic disabling and disfiguring skin lesions in CEP patients). In addition we have previously performed and published supportive work using a tool compound (a proteasome inhibitor termed in the data MG) to demonstrate that elevation of cellular levels of UROIIIS enzyme is associated with decreased skin lesions in a mouse in vivo model of CEP (Blouin et al. PNAS, 2013). We have also demonstrated that this tool compound MG in the human cellular model of CEP reduces toxic porphyrin levels supporting the observations from the in vivo model by FACS analysis of the cell lines (FIG. 3). The accumulation of porphyrins is measured by fluorescence spectroscopy (fluorocytes) and appear shifted to the right as compared to normal cells (which are concentrated in the left area). The numbers in bold indicate the percentage of cells in each of the specific populations. Clearly, the addition of Ciclopirox (coded 7D7) is able to largely restore the normal HEK cellular phenotype (i. e., reverse the CEP defect).

Figure 4:
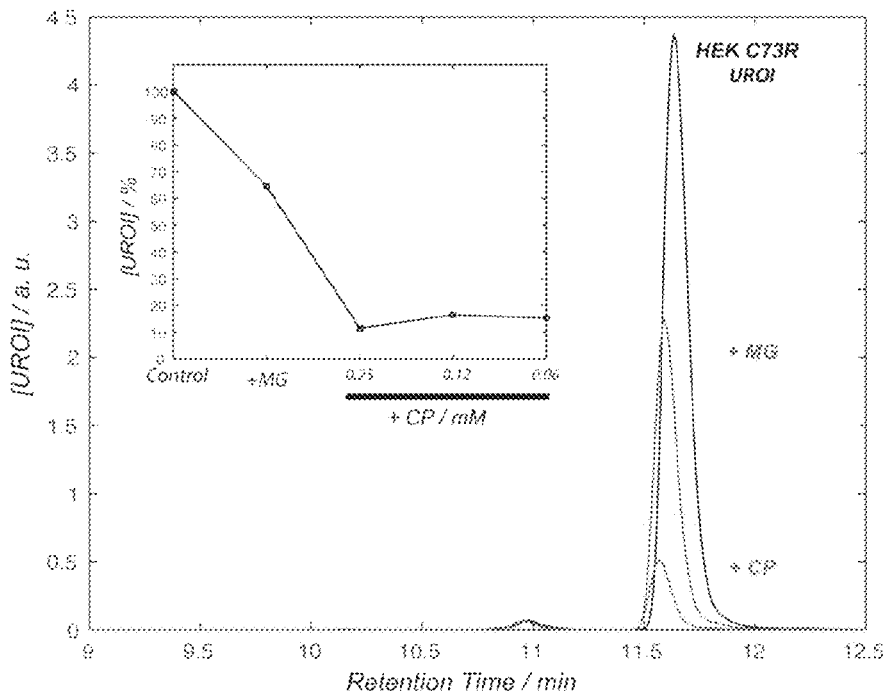
FIG. 4: HPLC cromatogram showing the reduction of UROI in the HEK 562 cells upon addition of equimolar quantities of MG and ciclopirox (CP). Inset: variation of the concentration of UROI as a function of the CP concentration, in comparison to MG and the absence of any chemical. CP=ciclopirox, MG=proteasomal inhibitor MG132, UROI=uroporphyrinogen I.

Moreover, the reduction in the fluorescence corresponds to a decrease in the intracellular concentration of UROI (see FIG. 4).

Figure 5:
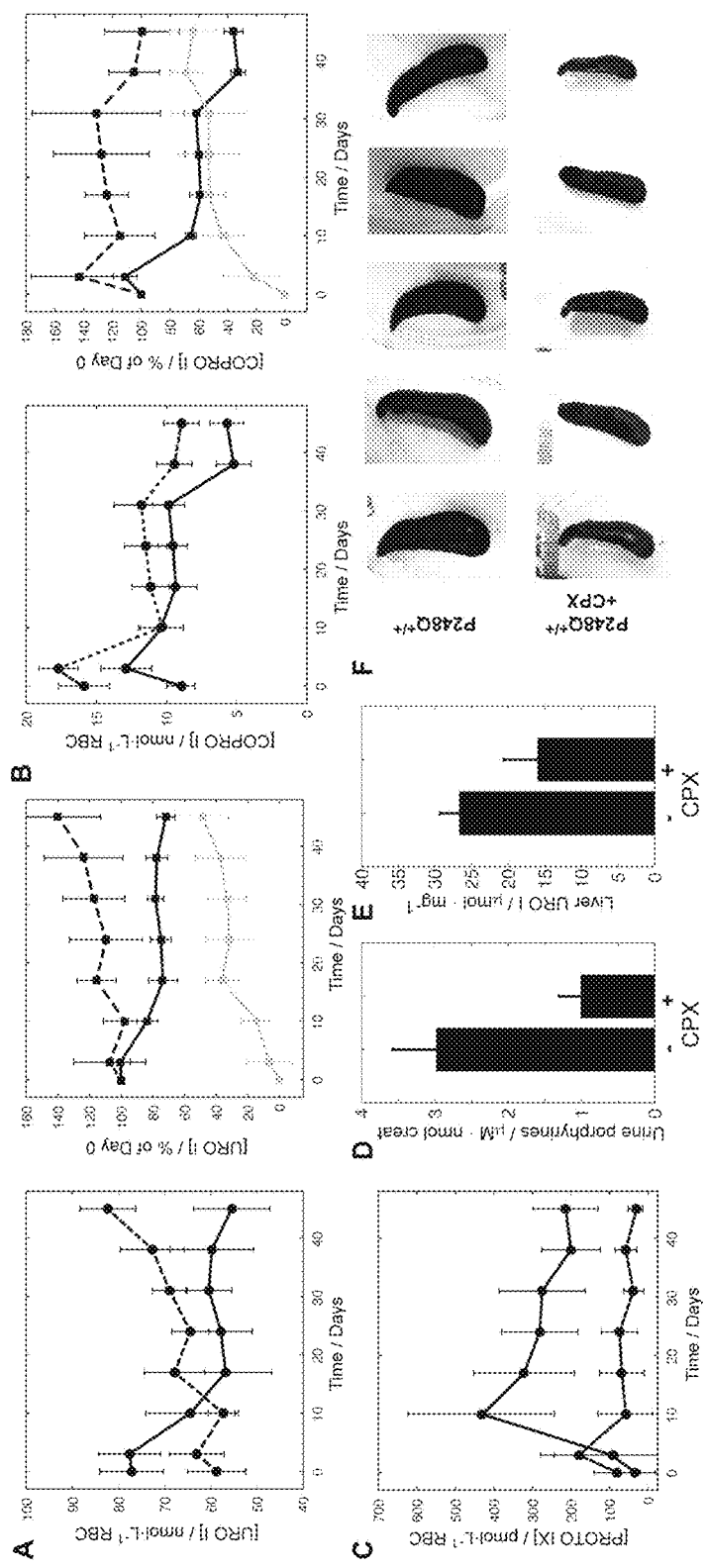
FIG. 5: Change in porphyrin levels and consequent effect on splenomegaly in mice treated with ciclopirox (CPX). A) Left: URO I or B) COPRO I porphyrin concentration in red blood cells (RBC) as determined by HPLC analysis for the mouse group treated with CPX (n=7, solid line) and the control group (n=9, dashed line). Right: representation of the same porphyrin levels but compared to their respective values at day 0 for the mice treated with CPX (solid line) and the untreated mice (dashed line). The reduction of porphyrins between the two groups is shown in grey dashed line (in percentage). C) Variation in the protoporphyrin IX (PROTO IX) concentration over time in the mouse group treated with CPX (solid line) and the control group (dashed line). D) Concentration of porphyrins in urine at day 45 of treatment (normalized versus creatinine concentration). E) Change in UROI levels in the liver at day 45 of treatment (weight normalized) F) CPX reduces splenomegaly after 45 days of treatment since the spleen volume of the untreated mice (top row) is higher than the CPX treated group (bottom row) Splenomegaly is directly associated with haemolytic anaemia.

4. Ciclopirox Reduces UROI Levels in Different Tissues of a Murine Model of CEP and Improves Splenomegaly:

As shown in FIGS. 5-A, -B and -D, isomer I porphyrins (URO I (A) and COPRO I (B) in the blood and urine (D) were significantly reduced in the group treated with ciclopirox when compared with the control group. The reduction in porphyrins in RBCs appeared to be greatest in the first 20 days following treatment, after which there was a slow-to-steady reduction until the last evaluation (day 45). Similar results were observed for the hepta-, hexa-, and penta-isomer I porphyrins (data not shown). Preliminary data suggests that ciclopirox would continue reducing the porphyrin levels after 45 days (if administration is continued). Upon treatment disruption, the porphyrin levels are restored, but slowly.

Remarkably, ciclopirox was able to increase the concentration of protoporphyrin IX (PROTO IX), an important precursor of the haem group downstream of UROIIIS activity, thus demonstrating the pharmacological chaperone activity in the mouse metabolism (FIG. 5-C). Additionally, after 45 days of treatment, ciclopirox reduced in 40% the porphyrin levels in liver tissue (shown in FIG. 5-E for UROI) and the splenomegaly (FIG. 5-F)—evidence of reduced haemolysis. Moreover, there was a significant weight reduction of the spleen when comparing the ciclopirox group (mean 410±86 mg, FIG. 5-F bottom row) and the untreated group (mean 985±204 mg, FIG. 5-F top row).

Materials and Methods

Obtaining and Purifying the Enzyme:

The enzyme is obtained and purified by following the method published by Millet 0 et al. (2009) Biochemistry 48: 454-461.

Enzymatic Assay:

The assay is based on the method described by Jordan (Shoolingin-Jordan P M et al. (1997). Methods in enzymology 281: 327-336) with some modifications. 5 mL of porphobilinogen deaminase (PBGD) at a concentration of 150 mM in 24 mL of buffer (20 mM Tris-HCl pH 8.0, NaCl 150 mM, pH 8.0) is add in a 96 weels plate. 12.5 mL of the porphobilinogen (PBG) substrate are then added, diluted to different concentrations (0.1, 0.4, 0.8, 1.5, 2, 3, 4 mM) in the aforementioned buffer and are incubated at 37° C. for one minute. A control assay containing a buffer without substrate (PBG) in the same proportions is performed at the same time. The enzymatic reaction is stopped by means of freezing the samples at −80° C., 10 min. Then the mixture is incubated again with 12.5 mL of 30 mM uroporphyrinogen 3 synthase (U3S) at 37° C. for 5 minutes to transform the preuroporphyrinogen into uroporphyrinogen III. If the assay is performed in the presence of a pharmacological chaperone, the latter is added in dissolved form into the buffer. The reaction is again stopped by means of freezing at −80° C. Then the formed $CO_2$ and uroporphyrinogens are oxidized to uroporphyrins by means of adding 12.5 mL of I2/KI solution and incubation for 10 minutes in ice and darkness. The iodine excess is then bleached by adding 12.5 mL of saturated sodium metabisulfite solution. 125 mL of 10% trichloroacetic acid (TCA) are added to precipitate the protein. Finally, we measure the change of absorbance at 405 nm with respect to the control sample in a plate ABS reader.

In Vitro Cellular Model of CEP:

50.000 K562 URO mutant cells/well are incubated in 250 mL of medium/well (RPMI media with 10% FBS). On the third day, the media is changed and the chaperone added in different concentration. The chaperone is incubated for 16-18 h at 37°. Finally, the effect of the chaperone is checked by fluorescence microscopy and by cytometer (FACS).

High Performance Liquid Chromatography (HPLC):

HPLC was used to separate and quantify UROI and UROIII products from PBGD and UROIIIS-C73N enzymatic assays and from cellular extracts. HPLC was carried out on a ODS Hypersil C18 column (5 um, 3×200 mm; Thermo Scientific, MA, USA). Porphyrins were separated with a 15 min isocratic elution in a mobile phase of 89% 1M ammonium acetate buffer pH 5.16 and 11% Acetonitrile, at a flow rate of 0.5 mL/min, and were detected by fluorescence with an excitation wavelength 405 nm and emission wavelength 610 nm, which is characteristic of porphyrins. The sample injection volume was 20 mL.

Animal Studies:

The CEP murine model is a bona fide model of human CEP since it shows the metabolic defect, reflected in the isomer I porphyrin accumulation in blood as well as skin lesion defects upon irradiation with UV light. A total of 16 animals (murine model of CEP) were used in the experiment and ciclopirox was mixed with the food pellets; 7 animals had food with ciclopirox (plasma levels achieved between 15 and 20 µM) and 9 animals were not given treatment. The isomer I porphyrin levels were monitored in the blood weekly. After a basal (pre-treatment) sample (day 0), treatment was started on day 2 and the first post-treatment sample was obtained on day 3, followed by weekly monitoring.

REFERENCES

Fortian A. et al. *Biochemistry*, 2009, vol. 48, 454-461.
Shoolingin-Jordan P. M. et al. *Methods in enzymology*, 1997, vol. 281, 327-336.
Bdira F et al. *Human Molecular Genetics*. 2014, 23, 5805-5813.
Fortian A. et al. *Journal of Biological Chemistry*, 2011, 286, 13127-13133.
Blouin J M, et al. *Proc. Natl. Acad. Sci. USA.*, 2013, 110, 18238-18243.

The invention claimed is:

1. A method for the treatment and/or prevention of congenital erythropoietic porphyria (CEP) in a subject, comprising administering a therapeutically effective amount of ciclopirox, or a pharmaceutically acceptable salt or solvate thereof, to said subject.

2. The method according to claim 1, wherein the salt is ciclopirox olamine.

3. A method for the treatment and/or prevention of congenital erythropoietic porphyria (CEP) in a subject, comprising administering to said subject a pharmaceutical composition comprising (i) a therapeutically effective amount of ciclopirox, or a pharmaceutically acceptable salt or solvate thereof, and (ii) a pharmaceutically acceptable excipient.

4. The method according to claim 3, wherein said administering comprises orally or topically administering said pharmaceutical composition.

5. The method according to claim 3, wherein said pharmaceutical composition is in a form of a lacquer, a shampoo, a solution, a suspension, a cream, a lotion, or a gel.

6. The method according to claim 4, wherein said pharmaceutical composition is in a form of a lacquer, a shampoo, a solution, a suspension, a cream, a lotion, or a gel.

* * * * *

UNITED STATES PATENT AND TRADEMARK OFFICE
CERTIFICATE OF CORRECTION

PATENT NO. : 10,420,755 B2
APPLICATION NO. : 16/326215
DATED : September 24, 2019
INVENTOR(S) : Millet Aguilar-Galindo et al.

It is certified that error appears in the above-identified patent and that said Letters Patent is hereby corrected as shown below:

On the Title Page

Item (30), under Foreign Application Priority Data:
"(EP)............ 6382493" should be -- (EP)........... 16382493.1 --.

Signed and Sealed this
Twenty-ninth Day of October, 2019

Andrei Iancu
*Director of the United States Patent and Trademark Office*